US00PP20345P2

(12) United States Plant Patent
Bedard

(10) Patent No.: US PP20,345 P2
(45) Date of Patent: Sep. 22, 2009

(54) MINIATURE ROSE PLANT NAMED 'WEKDOUDOU'

(50) Latin Name: *Rosa hybrida*
Varietal Denomination: WEKdoudou

(75) Inventor: Christian Bedard, Brea, CA (US)

(73) Assignee: Weeks Wholesale Rose Grower, Inc., Pomona, CA (US)

( * ) Notice: Subject to any disclaimer, the term of this patent is extended or adjusted under 35 U.S.C. 154(b) by 0 days.

(21) Appl. No.: 12/217,197

(22) Filed: Jul. 1, 2008

(51) Int. Cl.
*A01H 5/00* (2006.01)

(52) U.S. Cl. ..... Plt./116

(58) Field of Classification Search ..... Plt./116
See application file for complete search history.

*Primary Examiner*—Annette H Para
(74) *Attorney, Agent, or Firm*—Christie, Parker & Hale, LLP.

(57) ABSTRACT

A new variety of Miniature rose suitable for garden decoration, having flowers of smoky chocolate orange with a rust reverse coloration.

1 Drawing Sheet

Classification: The present invention relates to a new *Rosa hybrida* plant.

Variety denomination: The new plant has the varietal denomination 'WEKdoudou'.

BACKGROUND OF THE INVENTION

This invention relates to a new and distinct variety of Miniature Rose. It has as its seed parent the variety known as 'POUlclaus' (U.S. Plant Pat. No. 9,063) and as its pollen parent the variety known as 'WEKpaltlez' (U.S. Plant Pat. No. 15,155).

SUMMARY OF THE INVENTION

Among the features which distinguish the new variety from other presently available and commercial rose cultivars known to the inventor are the following combinations of characteristics: its unique flower coloration of smoky chocolate orange with a rust reverse, its red suffusion on the inner surface of the sepal that appears as the flower ages, its greyed purple anther internal part and its very glossy foliage. The plant has a bushy compact rounded growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKdoudou' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, 'POUlclaus' by the following combination of characteristics: whereas 'WEKdoudou' bears semi-double flowers (about 5 to 10 petals) of smoky chocolate orange with a rust reverse coloration, 'POUlclaus' bears semi-double flowers of deep red coloration with significantly heavier petalage (about 14 to 18 petals). The new variety has a bushy compact rounded low growing habit (about 42 to about 52 cm. in height and about 42 to about 52 cm. spread at the widest point), whereas the seed parent has a significantly taller and larger bushy, compact, upright growing habit (about 65 to about 75 cm. in height and about 65 to about 75 cm. spread at the widest point).

The new variety may be distinguished from its pollen parent, 'WEKpaltlez' by the following combination of characteristics: whereas 'WEKdoudou' bears semi-double flowers (about 5 to 10 petals) of smoky chocolate orange with a rust reverse coloration, 'WEKpaltlez' bears double flowers of smoky chocolate orange coloration overlaid with a wash of lavender with significantly heavier petalage (about 17 to 27 petals). The new variety is classified as a miniature rose with a bushy compact rounded low growing habit (about 42 to about 52 cm. in height), whereas the pollen parent is classified as a floribunda rose with a significantly taller bushy upright medium to tall growing habit (about 170 to about 210 cm. in height).

COMPARISON WITH THE CLOSEST COMMERCIALLY AVAILABLE CULTIVAR

The closest commercially available cultivar to the new variety is the pollen parent 'WEKpaltlez'.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of June. Phenotypic expression may vary with environmental, cultural and climatic conditions, as well as differences in conditions of light and soil.

FLOWER

The new variety sometimes bears its flowers singly, sometimes in clusters of two to four or more per stem. Flowers may be borne in regular rounded clusters on strong short stems (about 7 to about 18 cm.). Outdoors, the plant blooms abundantly and nearly continuously during the growing season. The flowers have a slight fruity fragrance.

BUD

The peduncle is about 1.8 to about 3.0 cm. in length, of average caliper (about 0.15 to about 0.2 cm. in diameter), and usually erect. It is mostly smooth, with few stipitate glands. Peduncle color is between 144A and 146A sometimes lightly suffused, especially on the side exposed to the sun, with between 187B and 183B.

Before the calyx breaks, the bud is about 0.7 to about 1.4 cm. in diameter at the widest point, about 1.1 to about 1.6 cm. in length, and pointed in shape. The surface of the bud bears some foliaceous appendages, some stipitate glands and hairs, usually with slender entire foliaceous parts extending beyond the tip of the bud about ¾ or more of its length. Bud color is between 137B and 146A often heavily suffused, especially on the side exposed to the sun, with between 187A and 183A.

The sepals are about 2.0 to about 2.4 cm. in length and about 0.5 to about 0.6 cm. in width at the widest point. The outer surface color of the sepal is between 137B and 146A often heavily suffused, especially on the side exposed to the sun, with between 187A and 183A. The inner surface color of the sepal is near 138A broadly bordered by near 139A. After the sepals open, the inner surface color is often moderately suffused, especially on the area exposed to the sun, with between 187A and 183A. The inner surface of the sepal is covered with fine wooly tomentum; sepal margins are lined with very few stipitate glands and numerous hairs.

The receptacle of the flower is of medium length (about 0.5 to about 0.6 cm.) and moderately thin in caliper (about 0.5 to about 0.6 cm. in diameter). The receptacle is urn-shaped to moderately globular in form. Its surface is very smooth with thick fleshy walls. The receptacle color is between 144A and 146A often moderately suffused, especially on the side exposed to the sun, with between 187B and 183B.

As the petals open (after the calyx breaks), the bud is about 1.1 to about 1.5 cm. in diameter at the widest point, about 1.5 to about 2.2 cm. in length, and moderately ovoid to somewhat pointed in form. The color of the under surfaces of the newly opened petals is between 46B and 53C. At the point where the petal attaches, there is a very small zone of between 4D and 2C. The color of the upper surface of the newly opened petals is between 42A and 45D often heavily blushed especially on the upper ⅓ of the petal with between 187A and 187B. At the point where the petal attaches, there is a small zone of between 3C and 4B.

BLOOM

When fully open, the bloom ranges from about 3.8 to about 5.9 cm. in diameter. Petalage is semi-double with about 5 to 10 petals and about 2 to 7 petaloids irregularly arranged. When partially open, the bloom form is somewhat high centered to moderately cupped, and the petals are loosely spiraled to cupped with petal edges moderately reflexed outward. When fully open, the bloom form is more cupped, and the petals are loosely cupped with petal edges very reflexed to somewhat rolled outward.

PETALS

The substance of the petals is moderately heavy and of somewhat thick thickness, with upper surfaces moderately velvety to somewhat satiny and under surfaces slightly shiny. The petals are about 1.6 to about 2.5 cm. in length and about 1.4 to about 2.7 cm. in width at the widest point. Petal margins are entire.

The outer petals are nearly round to somewhat obovate in shape with rounded apices.

The inner petals are nearly round to moderately obovate in shape with rounded apices.

Petaloids are about 0.9 to about 1.9 cm. in length and about 0.2 to about 1.7 cm. in width at the widest point. Petaloids are irregularly shaped moderately obovate to somewhat subulate with rounded apices.

NEWLY OPENED FLOWER

The under surface color of the outer, intermediate and inner petals is between 44B and 53C. At the point where the petal attaches, there is a very small zone of between 4D and 2C. The upper surface color of the outer, intermediate and inner petals is between 44B and 45D often heavily blushed especially on the upper ⅓ of the petal with between 187A and 187B. At the point where the petal attaches, there is a small zone of between 5C and 4B.

The under and upper surface color of the petaloids are similar in coloration to the upper and under surfaces of the intermediate and inner petals.

The general tonality of the newly opened flower is between 44B and 45D often heavily blushed especially on the upper ⅓ of the petal with between 187A and 187B.

THREE-DAY-OLD FLOWER

The under surface color of the outer, intermediate and inner petals is between 45C and 53C. At the point where the petal attaches, there is a very small zone of between 155A and 155C. The upper surface color of the outer, intermediate and inner petals is between 44B and 47B often heavily blushed especially on the upper ⅓ of the petal with between 187A and 187B. At the point where the petal attaches, there is a small zone of between 155A and 155C.

The under and upper surface color of the petaloids are similar in coloration to the upper and under surfaces of the intermediate and inner petals.

The general tonality of the three-day-old flower is between 44B and 47B often heavily blushed especially on the upper ⅓ of the petal with between 187A and 187B.

On the spent bloom, the petals usually drop off cleanly.

In June in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are average in number (average about 70) and are arranged regularly about the pistils; a few are mixed with petaloids. The filaments are of medium length (about 0.4 to about 0.6 cm.) most with anthers. Filaments are between 5A and 6A in color sometimes lightly suffused with between 46B and 44B. The anthers are moderately large for the class and all open approximately at the same time. Anther color when immature is near 23B on the external part and near 187D on the internal part. Anther color at maturity is near 165D on the external part and near 187B on the internal part. Pollen is somewhat sparse and near 18C in color.

FEMALE REPRODUCTIVE ORGANS

Pistils vary in number (average about 35). The styles are somewhat uneven, average in length (about 0.4 to about 0.6 cm.), moderately thin in caliper, and loosely bunched. Stigma color is between 159A and 164D. Style color is between 4D and 150D usually heavily suffused with between 60A and 59B. Ovaries are usually all enclosed in the calyx.

Hips have not been observed on this variety when grown in Pomona, Calif.

FOLIAGE

The compound leaves are usually comprised of three to seven leaflets and are borne abundantly. The five-leaflet leaves are about 5.5 to about 10.2 cm. in length and about 3.4 to about 7.1 cm. in width at the widest point, somewhat heavy to moderately crisp in texture and very glossy in finish. The terminal leaflets are about 2.2 to about 4.3 cm. in length and about 1.4 to about 2.5 cm. in width at the widest point, shaped moderately oval to somewhat ovate with acute apices and rounded bases. Their margins are usually simply serrate.

The upper surface color of the mature leaf is between 139A and 147A. The under surface color of the mature leaf is between 147B and 146A. The upper surface color of the young leaf is between 146A and 146B, sometimes lightly suffused especially on the edge with between 187B and 187C. The under surface color of the young leaf is between 147B and 146B, sometimes lightly suffused with between 187B and 187C.

The rachis is moderately light to average in caliper and somewhat rough. The upper side is shallowly grooved with few hairs and some stipitate glands on the edges of the grooves. The under side of the rachis is somewhat rough with very few stipitate glands and few small prickles. The rachis color is near 146C on the under side and near 146B on the upper side sometimes moderately suffused with between 187B and 187C.

The stipules are about 0.5 to about 1.3 cm. in length and moderately wide (about 0.3 to about 0.6 cm.) with medium length straight points that usually turn out at an angle of more than 45 degrees and sometimes recurve toward the stem. The stipule color is between 146C and 146B sometimes moderately suffused with between 187B and 187C.

The petiole is moderately light to average in caliper and somewhat rough. The upper side is shallowly grooved with few hairs and some stipitate glands on the edges of the grooves. The under side of the petiole is somewhat rough with very few stipitate glands and few small prickles. The petiole is about 0.9 to about 1.6 cm. in length and about 0.1 to about 0.15 cm in diameter at the widest point. The petiole color is near 146C on the under side and near 146B on the upper side sometimes moderately suffused with between 187B and 187C.

The plant displays an average degree of resistance to powdery mildew and rust as compared to other commercial varieties grown under comparable conditions in Pomona, Calif. The plant's winter hardiness and drought/heat tolerance are yet to be determined.

GROWTH

The plant has a bushy compact rounded low growing habit (about 42 to about 52 cm. in height and about 42 to about 52 cm. spread at the widest point), with full branching. It displays moderately vigorous growth and the canes are of somewhat heavy caliper for the class.

The color of the major stems is between 146B and 147B. They bear some large prickles that are about 0.6 to about 1.0 cm. in length. The large prickles are almost straight to angled slightly downward with a somewhat short broad oval base; prickle color is between 165C and 166D. The major stem bears very few small prickles of similar shape and coloration.

The color of the branches is near 146A sometimes lightly suffused with between 187C and 183C. They bear few medium size prickles which are of similar shape to the large prickles on the major stems. The medium prickles are about 0.5 to about 0.6 cm. in length. Prickle color is between 187B and 187C. The branches bear no small prickles.

The color of the new shoots is between 146B and 146A sometimes lightly suffused with between 187C and 183C. They bear few medium size prickles which are of similar size and shape to the medium size prickles on the branches; prickle color is between 187B and 187C. The shoots bear no small prickles.

I claim:

1. A new and distinct Miniature rose plant of the variety substantially as described and illustrated herein.

* * * * *

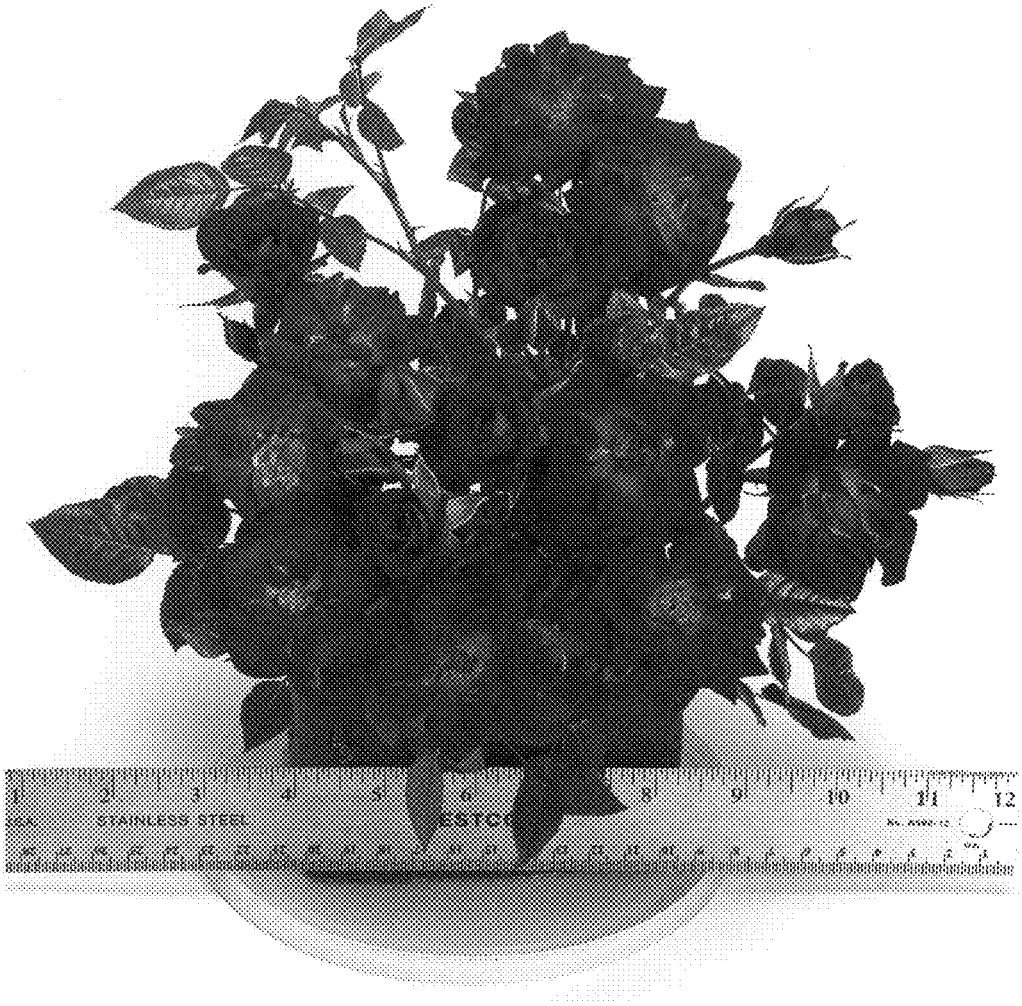
STAINLESS STEEL